United States Patent [19]

Aken et al.

[11] Patent Number: 5,264,370
[45] Date of Patent: Nov. 23, 1993

[54] DETECTION OF BASEMENT MEMBRANE COMPONENTS AS DIAGNOSTIC OF CANCER AND OTHER DISEASES

[75] Inventors: Morgan V. Aken; Stefan L. Paskell, both of Bainbridge Island, Wash.

[73] Assignee: Bainbridge Laboratories, Inc., Bainbridge Island, Wash.

[21] Appl. No.: 721,756

[22] Filed: Jun. 26, 1991

Related U.S. Application Data

[63] Continuation-in-part of Ser. No. 283,397, Dec. 12, 1988, abandoned.

[51] Int. Cl.$^5$ .......................................... G01N 33/566
[52] U.S. Cl. .................................... 436/501; 436/503; 436/536
[58] Field of Search ................. 436/536; 435/501, 503, 435/536

[56] References Cited

U.S. PATENT DOCUMENTS

| | | |
|---|---|---|
| 4,264,766 | 4/1981 | Fischer . |
| 4,340,581 | 7/1982 | Timpl . |
| 4,376,110 | 3/1983 | David et al. . |
| 4,452,901 | 6/1984 | Gordon et al. . |
| 4,497,900 | 2/1985 | Abram et al. . |
| 4,565,789 | 1/1986 | Liotta et al. . |
| 4,609,629 | 9/1986 | Timpl . |
| 4,628,027 | 12/1986 | Gay . |
| 4,689,220 | 8/1987 | Sturmer . |
| 4,847,199 | 7/1989 | Snyder et al. . |

FOREIGN PATENT DOCUMENTS

3743402A1  7/1988  Fed. Rep. of Germany .

OTHER PUBLICATIONS

Alitalo et al., *Int. J. Cancer* 27:755-761, 1981.
Askenasi, *J. Lab. Clin. Med.* 83(4):673-679, 1974.
Babaian et al., *J. Urol.* 131:463, 1984.
Barsky et al., *Lab Invest.* 49:140-147, 1983.
Bisbee and Kelleher, *Clin. Chim. Acta* 90:29-36, 1978.
Bowen-Pope et al., *Proc. Natl. Acad. Sci. USA* 81:2396-2400, 1984.
Bowman et al., *J. Biol. Chem.* 255:9484-9498, 1980.
Brocks et al., *Diabetologia* 28:929, 1985.
Brocks et al., *Clin. Chem.* 32:787, 1986.
Brooks et al., *Clin. Exp. Immunol.* 39:477-485, 1980.
Brown et al., *J. Biol. Chem.* 255:4980-4983, 1980.
Burtin, *Int. J. Cancer* 30:13-20, 1982.
Cederholm et al., *Proc. Natl. Acad. Sci. USA* 83:6151-6155, 1986.
Conn et al., *Br. J. Urology* 60:536, 1987.
Csako et al., *Clin. Exp. Immunol.* 44:181-190, 1981.
Csako et al., *Exp. Eye Res.* 36:403-414, 1983.
Dixit, *Connective Tissue Research* 14:31-30, 1985.
Dresden et al., *Cancer Research* 32:993-996, 1972.
Eeckhout et al. *FEBS Lett.* 107:69-72, 1979.
Fessler et al., *J. Biol. Chem.* 259:9783-9789, 1984.
Galfre et al., *Nature*, 277;131-133, 1979.
Garbisa et al., *Cancer Letters* 9:359-366, 1980.
Huang et al., *Biochim. Biophys. Acta* 570:149-156, 1979.
Knudsen, *Anal. Biochem.* 147:285-288, 1985.
Kobyashi et al., *Urol. Int.* 39:232, 1984.
Kohler and Milstein, *Eur. J. Immunol.* 6:511-519, 1976.
Kohler and Milstein, *Nature* 256:495-497, 1975.
Krane et al., *J. Clin. Invest.* 59:819-827, 1977.
Liotta et al., *Ann. Rev. Biochem.* 55:1037-1057, 1986.
Liotta et al., *Biochemistry* 20:100-104, 1981.
Liotta et al., *J. Natl. Cancer Inst.* 58:1427-1431, 1977.

(List continued on next page.)

*Primary Examiner*—Sam Rosen
*Attorney, Agent, or Firm*—Seed and Berry

[57] ABSTRACT

Methods for the diagnosis of diseases that result in the release of fragments of basement membrane, including fragments, intact molecules and/or complexes of basement membrane components, are disclosed. Detection of basement membrane fragments, intact molecules and/or complexes in a biological fluid by the immunological and physicochemical methods of the present invention allows the diagnosis of a variety of diseases, including cancers, collagen degenerative diseases, and hepatitis. Suitable biological fluids include urine, serum, synovial fluid, and cerebrospinal fluid.

6 Claims, 7 Drawing Sheets

OTHER PUBLICATIONS

Liotta et al., *Nature* 284:67–68, 1980.
McCabe et al., *Cancer Res.* 44:5886, 1984.
McCarthy et al., *Biochemistry* 27:1380–1388, 1988.
Mellon et al., *Biochem. Genet.*, 22:631–640, 1985.
Nagai et al., *Biochim. Biophys. Acta* 967:176, 1988.
Nakajima et al., "Basement membranes degradative enzymes as possible markers of tumor metastasis," in *Cancer Metastasis: Experimental and Clinical Strategies*, Alan R. Liss, Inc., 1986, pp. 113–122.
Palm et al., *Biochemistry* 24:7753–7760, 1985.
Pernice and Sedlacek, *J. Immu. Methods* 28:33, 1979.
Prockhop and Kivirikko, "Hydroxyproline and the Metabolism of Collagen," in B. S. Gould, ed., *Treatise on Collagen*, vol. 2A, Academic Press, pp. 215–246.
Raines and Ross, *J. Biol. Chem.* 257:5154–5160, 1982.
Rao et al., *Fed. Proc.* p. 418, Abstr. No. 44.
Rao et al., *Biochem. Biophys. Res. Commun*, 28:45, 1985.
Robertson and Williams, Nature 221:259, 1969.
Rohde et al., *Eur. J. Biochem.* 102:195–201, 1979.
Rucklidge et al., *Collagen Relat. Res.* 6:185–194, 1986.
Salo et al., *Int. J. Cancer* 30:699–673, 1982.
Savolainen et al., *Biochem. J.* 249:753–757, 1988.
Schneider et al., *Renal. Physiol.* 6:157–162, 1983.
Skubitz et al., *Exp. Cell Res.* 173:349–369, 1987.
Skubitz and Furcht, *J. Cell Biol.* 103(5):94a, 1986.
Stanker et al., *J. Immunol. Meth.* 76:157–169, 1985.
Starkey et al., *Cancer Research* 44:1585–1592, 1984.
Steinberg et al., *J. Cell Biol.* 87(2):304–308, 1980.
Takahashi et al. *J. Urol.* 138:207, 1987.
Taubman et al., *Proc. Soc. Exp. Biol. Med.* 152:284–287, 1976.
Thorgeirsson et al., *Int. Rev. Exp. Pathol.* 27:203, 1985.
Timpl et al., *J. Biol. Chem.* 254:9933–9937, 1979.
Towbin et al., *Proc. Natl. Acad. Sci. USA* 76:4350–4354, 1979.
Vartlo et al., *J. Ummunol. Meth.* 55:309–318, 1982.
Wajsman et al., *Urology* 12:659, 1978.
Weiss and Klain, *J. Clin. Invest.* 48:1–10, 1969.
Zimmerman and Vienken, *J. Membrane Biol.* 67:165–182, 1982.
Zucker et al., *Br. J. Cancer* 52:223–232, 1985.
Oellerich, "Enzyme-Immunoassay: A Review," *J. Clin. Chem. Clin. Biochem.* 22:895–904 (1984).
*The Sigma Chemical Co.*, St. Louis, Mo. p. 1027 (1986).
Albrechtsen et al. Cancer Reserach vol. 41 (Dec. 1981), pp. 5076–6079.
Yee et al. Cancer Research vol. 46 (Apr. 1986) pp. 1835–1839.

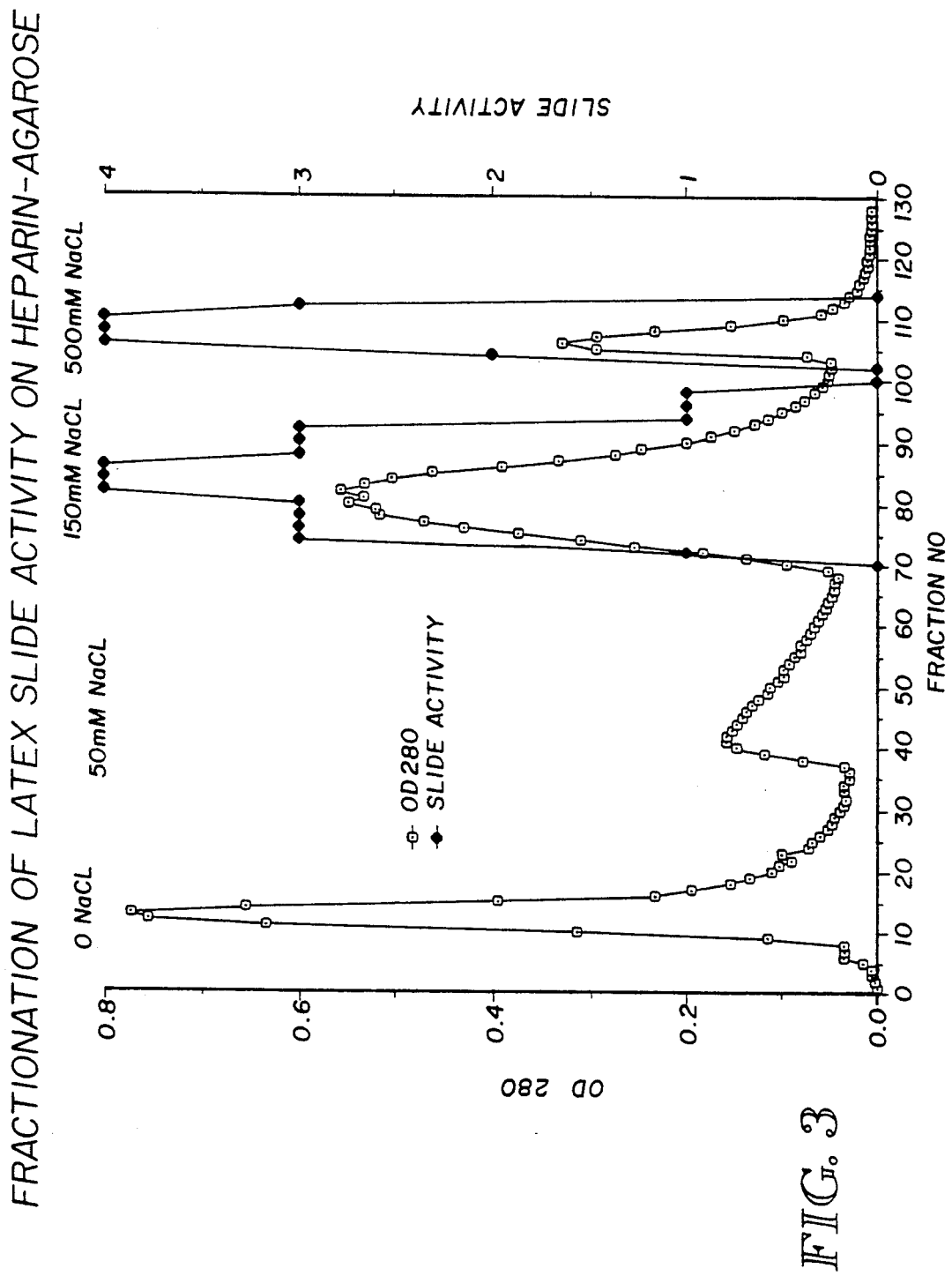

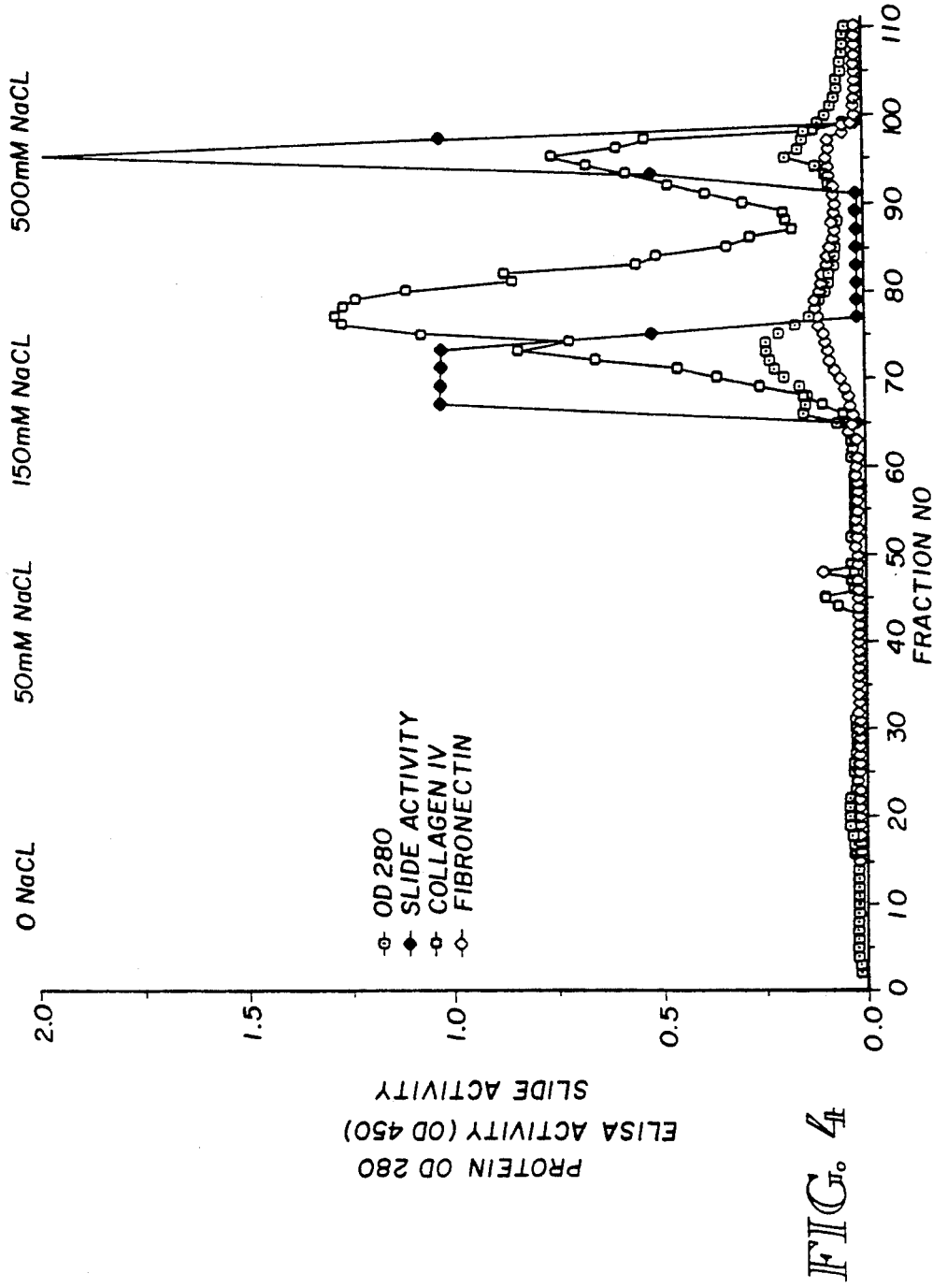

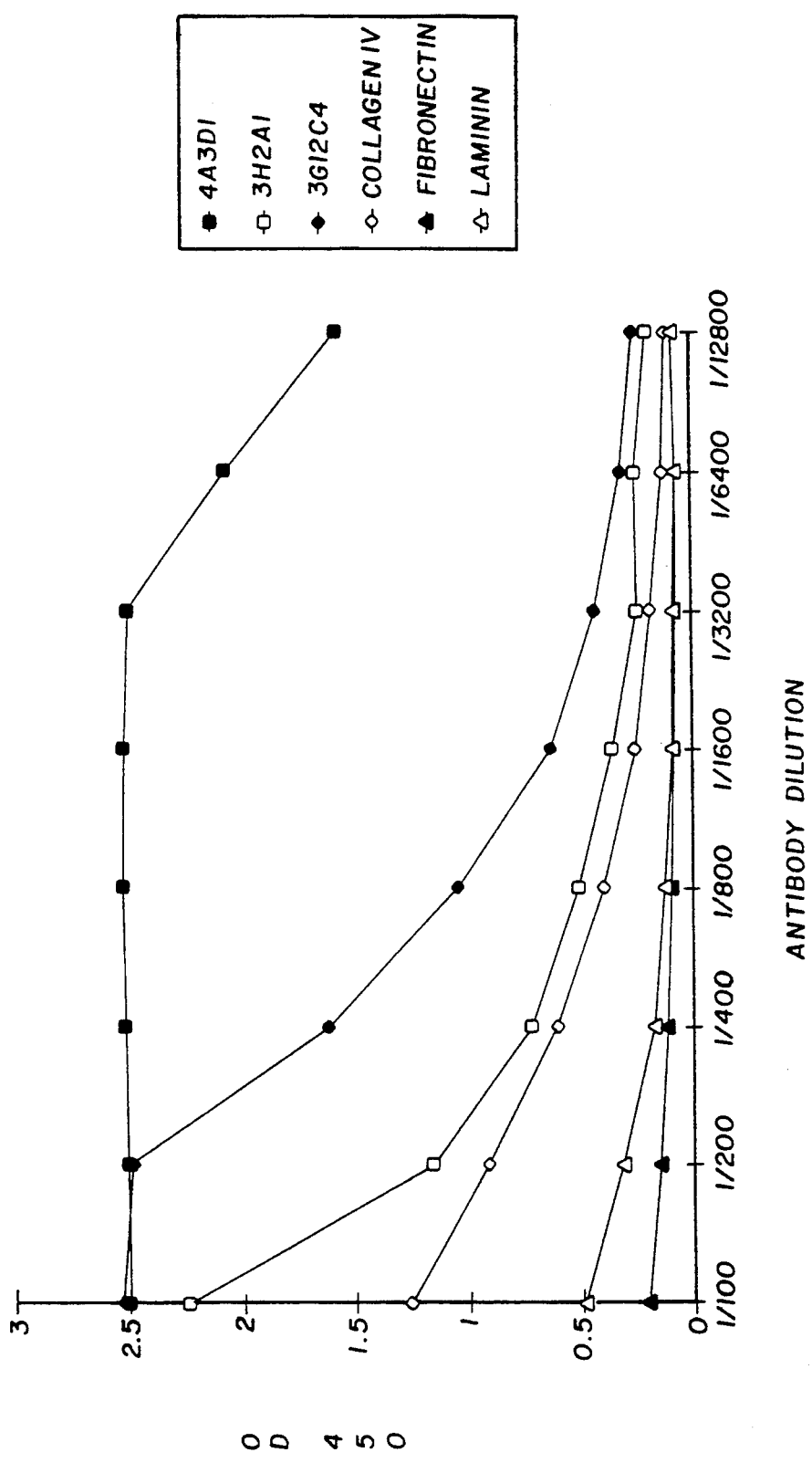

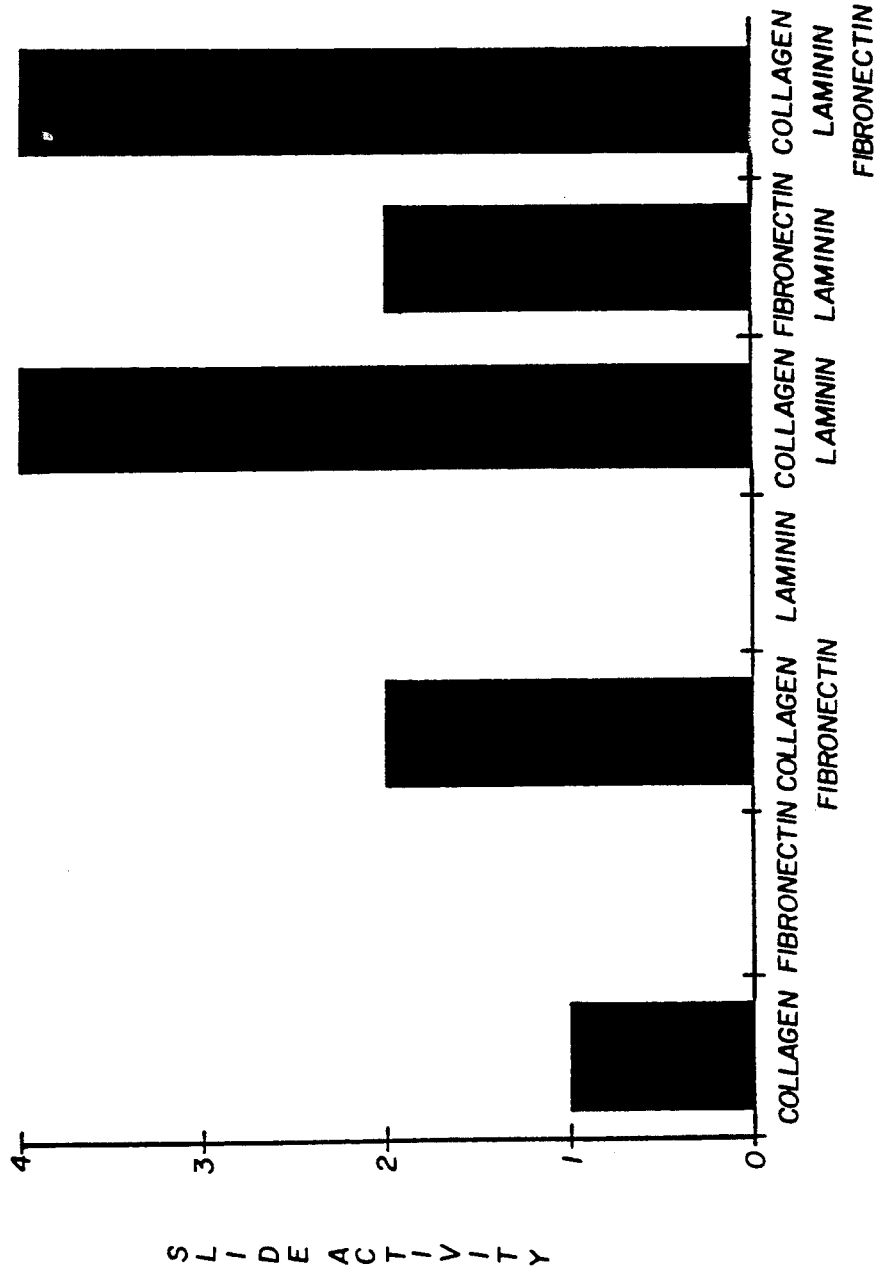

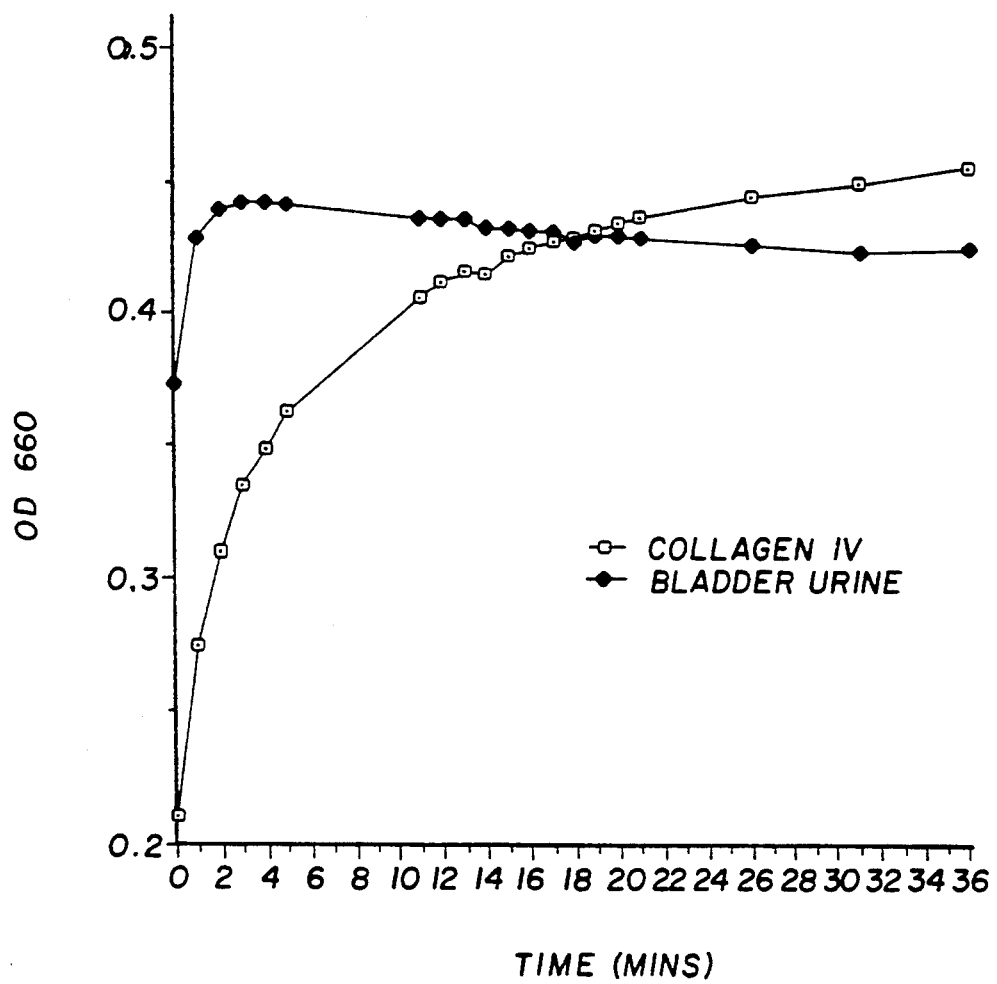

DETECTION OF BASEMENT MEMBRANE COMPONENTS AS DIAGNOSTIC OF CANCER AND OTHER DISEASES

CROSS REFERENCE TO RELATED APPLICATION

This application is a continuation-in-part application to Ser. No. 283,397, filed Dec. 12, 1988, now abandoned.

TECHNICAL FIELD

The present invention relates generally to the diagnosis of diseases, such as cancer, that result in the release of basement membrane fragments, including fragments, intact molecules and/or complexes of basement membrane components. This invention is more particularly related to detection of such fragments, intact molecules and/or complexes, by physicochemical and immunological methods.

BACKGROUND OF THE INVENTION

A challenge to medicine since its inception has been the development of methods that permit rapid and accurate detection of diseases. Despite advances in diagnostic technology over the years, the current techniques for the diagnosis of many diseases are either inadequate or cost prohibitive for wide scale application. One such illustrative disease is bladder cancer.

As a worldwide problem, it is estimated that there are 50,900 new cases of bladder cancer per year in Western Europe, 3,700 in Japan and 34,000 in North America (WHO 1984), with at least 3 to 4 times this number of patients attending hospitals for follow-up or treatment.

Bladder cancer occurs in two major forms: superficial and invasive. About 70% of superficial tumors will develop one or several recurrences during a five year follow-up period. The major risk is that the tumor will become invasive.

The invasive form of bladder cancer accounts for approximately 20%–30% of all bladder cancer. Invasive bladder cancer starts in the mucosa lining the bladder, invades through the basement membrane to reach muscle wall, and finally the pelvic tissues and surrounding organs, including local lymph nodes. The outlook depends on the stage, with five-year survivals from 11%–60%. The treatment is by radiotherapy, chemotherapy and surgery.

Patients with invasive bladder tumors are monitored by cytology and check cystoscopy. Although cytology is a noninvasive and less difficult procedure, it can be prone to error or uncertainty. For example, a positive result by cytology may be helpful, but a negative result cannot be taken as evidence of the absence of a tumor. Further, the reporting varies greatly with the cytologists' experience. Cystoscopy is an invasive, expensive and occasionally hazardous procedure, as it is frequently carried out under anesthesia. Despite the uncertainties associated with cystoscopic checks, they are nevertheless still considered by many medical practitioners as the diagnostic tool of choice because of the absence of better tests.

It is generally agreed that reliable tests for the presence of invasive bladder cancer would be helpful not only for initial detection, but also for recurrence and thus aid in the management of patients with histologically proven bladder cancer. If such a reliable test became available, it might then be used to screen persons at risk, e.g., men over 60 years of age. Further, a test not dependent upon gross visualization of a tumor should allow detection at an earlier stage.

Various tumor markers have been evaluated for their potential as tools in the diagnosis of bladder cancer. Positive serum tests for tumor markers, such as carcinoembryonic antigen (CEA), are usually restricted to advanced tumors. Furthermore, urinary infection has been shown to cause false positives.

In addition to the use of tumor markers, several alternative approaches to diagnosing bladder cancer have been suggested. For example, several urinary enzymes have been described with increased urinary activity in bladder cancer. However, none have been found to be useful in screening test. Similarly, although antibodies against urothelium and its tumors were at first thought to be tissue-specific, some were later shown to be oncodevelopmental antigens.

Although the inadequacies and problems in the diagnosis of one particular type of cancer are the focus of the preceding discussion, bladder cancer is merely a representative model. The diagnosis of numerous other diseases, including other types of cancer as well as non-cancer conditions, have similar problems.

Thus, there is a need in the art for a method of detecting diseases, such as cancers, that is rapid, accurate, cost-effective, and convenient. The present invention fulfills these needs and further provides other related advantages.

SUMMARY OF THE INVENTION

Briefly stated, the present invention provides methods for the detection of a disease that results in the release of fragments, intact molecules and/or complexes of one or more basement membrane components. These physicochemical methods generally comprise the steps of contacting a biological fluid with a suspension of microparticles which agglutinate in the presence of fragments, intact molecules and/or complexes of basement membrane components, and subsequently detecting the presence or absence of agglutination of the suspension of microparticles, thereby determining the presence or absence of the disease.

Within a related aspect, the invention provides another method for the detection of a disease that results in the release of basement membrane fragments, including fragments, intact molecules and/or complexes of one or more basement membrane components. This method generally comprises the steps of contacting a biological fluid with an antibody specific for a complex of one or more basement membrane components, and subsequently detecting the presence or absence of one or more immunocomplexes formed between the antibody and the complex, thereby determining the presence or absence of the disease.

Other aspects of the invention will become evident upon reference to the following detailed description and attached drawings.

BRIEF DESCRIPTION OF THE DRAWINGS

FIG. 3 graphically depicts fractionation of latex slide activity on Heparin agarose. Latex agglutination reactive fractions (after fractionation on 4% agarose) were pooled, dialyzed and applied to a Heparin agarose column. The column was sequentially eluted with 20 mM phosphate buffer (pH 7.4) containing 0, 50, 150 and 500 mM NaCl.

FIG. 4 graphically depicts fractionation of the 500 mM Heparin agarose fraction on DEAE-Biogel A. The 500 mM fraction from the Heparin agarose chromatography was further purified on DEAE-Biogel A. The column was sequentially eluted with 0, 50, 150 and 500 mM NaCl.

FIG. 5 graphically depicts the reactivity of the 150 mM DEAE-Biogel A fraction with different antibodies. The 150 mM fraction eluted from DEAE-Biogel A was tested with anti-collagen IV, anti-fibronectin, anti-laminin, and three monoclonal antibodies derived by screening against the 4% agarose fraction.

FIG. 6 graphically illustrates the reactivity of mixtures of basement membrane components in an agglutination assay. Concentrations of laminin and fibronectin were chosen such that they had no agglutination reaction on their own.

FIG. 7 graphically illustrates time courses of reactivity in an agglutination assay of collagen Type IV versus urine from a patient with bladder cancer.

DETAILED DESCRIPTION OF THE INVENTION

Prior to setting forth the invention, it may be helpful to an understanding thereof to set forth definitions of certain terms to be used hereinafter.

Complex—as used herein, includes the association of one or more intact basement membrane components, fragments thereof, or combinations of fragments and intact components.

Antibody—as used herein, includes both polyclonal and monoclonal antibodies; and may be an intact molecule, a fragment thereof, or a functional equivalent thereof; and may be genetically engineered. Examples of antibody fragments include F(ab')2' Fab', Fab and Fv.

As noted above, the present invention provides methods for the detection of diseases that result in the release of fragments, intact molecules and/or complexes of one or more basement membrane components. Basement membranes are extracellular matrices separating organ parenchymal cells from connective tissue mesenchyme. Normally, parenchymal cells and stroma cells remain oriented on their respective side of the basement membrane, even during organ development and tissue repair. Certain diseases are capable of disrupting basement membranes. For example, invasive tumor cells invade and traverse epithelial and endothelial basement membrane during the successive stages of the metastatic process. Local disintegration of the basement membrane is one of the initial events in the metastatic process and occurs at the membrane's region of contact with invading tumor cells.

The basement membrane (also referred to as basal lamina) is comprised of at least several identified proteins and peptide derivatives, including several specific types of collagen (e.g., Type IV and Type V), laminin, various types of cell adhesion molecules (CAMs), proteoglycans, and fibronectin. Basement membrane components and fragments thereof are released by the action of invasive tumors. Presumably, proteolytic enzymes secreted by tumor cells, or on their outer surface membrane, are responsible for this action (Salo et al., *Int. J. Cancer* 30:669–673, 1982; Garbisa et al., *Cancer Lett.* 9:359–366, 1980). Following release, fragments of basement membrane components may undergo further degradation, enzymatic or otherwise, which results in smaller fragments.

Figure 1:
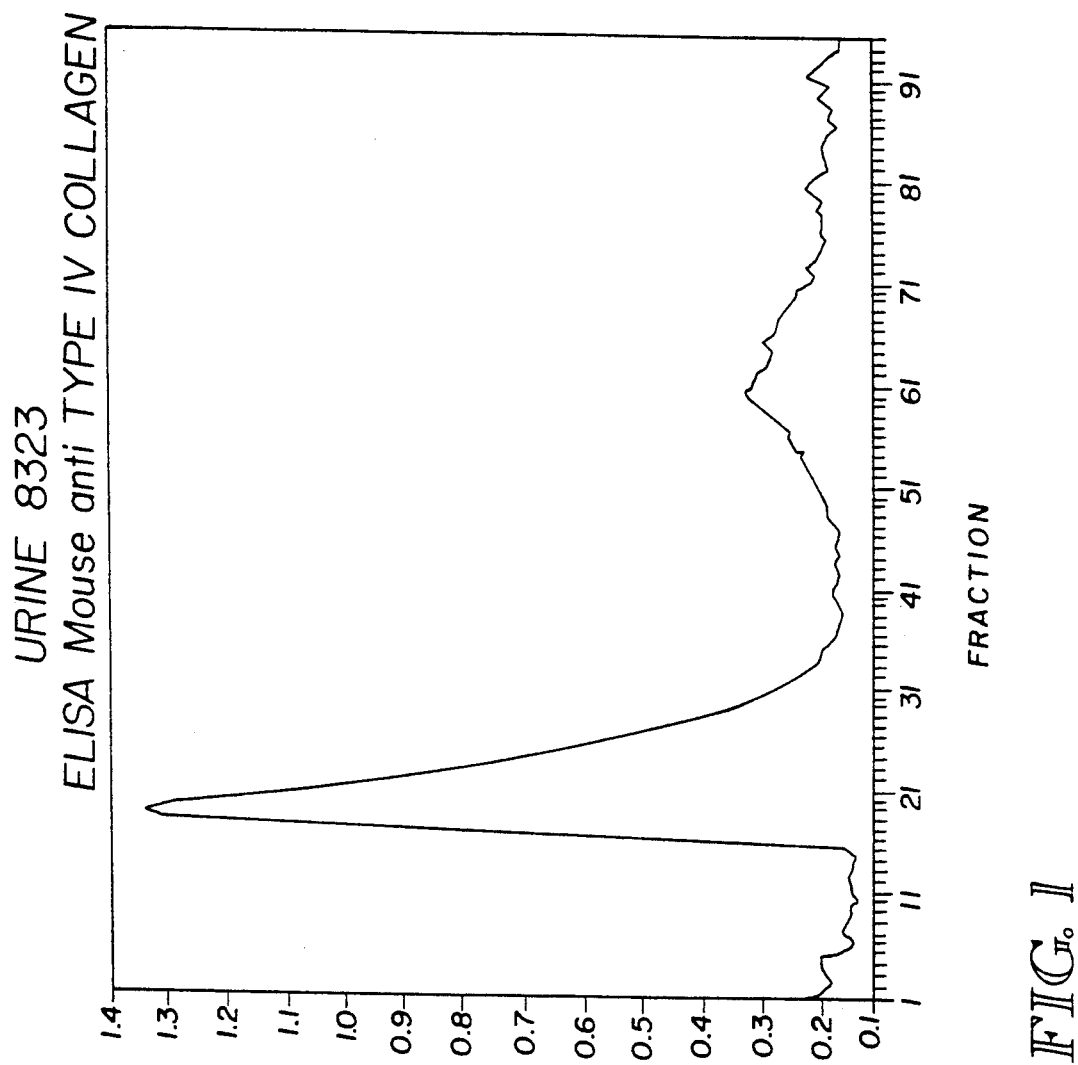
FIG. 1 is an elution profile of a bladder cancer patient's urine subjected to gel filtration chromatography on 4% agarose.

In addition to smaller fragments, complexes of basement membrane components have been found within the present invention to survive in detectable concentrations in the biological fluids of patients possessing an invasive cancer. For example, fractionation of the urine from a patient with bladder cancer and from a normal individual (FIGS. 1 and 2, respectively) by gel filtration chromatography reveals that only urine from the cancer patient has immunoreactive basement membrane-derived material with a relative molecular weight of at least about $1.5 \times 10^6$. Additional characterization (e.g., FIGS. 3 and 4) of this high molecular weight material indicates the presence of basement membrane-derived material, represented by collagen and laminin. Since the molecular weight observed is in excess of these components of basement membrane, complexes are present.

There exist at least two explanations for the appearance of complexes of basement membrane components in the body fluids of patients with invasive cancer. First, disintegration of the basement membrane by an invading tumor may result in the release of complexes of basement membrane components. These complexes represent molecules remaining attached by the same association whereby structural integrity is maintained in the intact membrane. Such complexes may be composed of one type of basement membrane component, more than one type of basement membrane component, and/or fragments of either. Second, disintegration of the basement membrane by an invading tumor may result in the release of individual basement membrane components and/or fragments thereof. Complexes may then be formed by their association subsequent to release from cells.

The association of basement membrane components and/or fragments subsequent to their release, to form complexes, may result from nonspecific interactions, such as hydrophobic interactions between nonpolar amino acid residues. Other interactions promoting this association may be of a more specific nature, such as the affinity of fibronectin and collagen for each other. Consequently, complexes composed of one type of basement membrane component, as well as complexes of fragments of more than one type of basement membrane component, may be formed following degradation of a basement membrane by a tumor. For example, a complex may contain only collagen (and/or collagen fragments) or it may contain a mixture of collagen and fibronectin (and/or their fragments).

The uniqueness of a particular complex, or particular fragment, may derive from the specific organ or specific tumor involved or both. The composition of basement membrane is likely to vary from organ to organ, e.g., basement membrane from neural cells contains a unique cell adhesion molecule, n-CAM. Similarly, different tumor cell lines may express different proteases utilized in metastases.

Another possible source of basement membrane components and/or fragments is the tumor cell. Certain tumor cells have been shown to secrete basement membrane proteins in vitro (Alitalo et al., *Int. J. Cancer* 27:755–761, 1981). It is possible that one or more of the basement membrane components secreted by tumor cells is a portion of the basement membrane complexes formed.

As noted above, the present invention, in addition to a physicochemical method, provides an immunological method for the detection of a disease that results in the release of basement membrane fragments, including fragments, intact molecules and/or complexes of one or more basement membrane components. This method generally comprises first contacting a biological fluid with an antibody specific for a fragment of a basement membrane component or a complex of one or more basement membrane components. Subsequently, the presence or absence of one or more immunocomplexes formed between the antibody and the fragment or complex is detected, thereby allowing a determination of the presence or absence of the disease.

Diseases other than invasive cancers can also result in the release of fragments, intact molecules and/or complexes of basement membrane components. For example, such fragments, intact molecules and/or complexes may be detected in patients with collagen degenerative diseases or hepatitis. Representative diseases which may be detected by this method include cancers, collagen degenerative diseases, and hepatitis. Examples of detectable cancers include urogenital, melanoma, lung and breast cancers. Urogenital cancers include bladder and prostate cancers.

The type of biological fluid in which the fragments accumulate is dependent chiefly on the location of the disease. For example, urine and serum are preferred for urogenital cancers, and cerebrospinal fluid for brain tumors. It would be evident to one skilled in the art to associate a particular biological fluid with a particular disease. Representative types of biological fluids include urine, serum, synovial, and cerebrospinal fluid. Particularly preferred are urine and serum.

Although polyclonal antibodies are suitable in the methods of the present invention, monoclonal antibodies are preferred. Because the tumor is producing fragments of the basement membrane components, potential antigenic sites which are not accessible on the intact component may be created or become exposed on a fragment. Such newly created or exposed antigenic determinants may be termed "neoantigenic determinants." Within the present invention, monoclonal antibodies may be produced that are specific for a fragment of a basement membrane component, such as collagen. In addition, because at least some of the basement membrane components, or fragments thereof, are in the form of complexes, new antigenic sites may be formed. Within the present invention, monoclonal antibodies are produced to such basement membrane complexes.

Polyclonal antibodies may be produced by immunization of an animal and subsequent collection of its sera. It is generally preferred to follow the initial immunization with one or more booster immunizations prior to sera collection. Monoclonal antibodies are generally produced by the method of Kohler and Milstein (*Nature* 256:495–497, 1975; *Eur. J. Immunol.* 6:511–519, 1976). Briefly, the lymph nodes and/or spleens of an animal injected with a basement membrane fragment or complex of fragments are fused with myeloma cells to form hybrid cell lines ("hybridomas" or "clones"). Each hybridoma secretes a single type of immunoglobulin specific for the fragment or fragment complex and, like the myeloma cells, has the potential for indefinite cell division.

A purified basement membrane fragment or complex ("basement membrane preparation") is used for the immunization. Preferably, the animals are immunized with at least 100 ng each of the basement membrane preparation, most preferably greater than 500 ng each. For immunization, the basement membrane preparation may be adsorbed to a solid phase matrix, preferably to nitrocellulose paper. The paper is then introduced into the animal. Techniques for introduction of the adsorbed antigen preparation include implantation (U.S. Pat. No. 4,689,220) or solubilization of the solid phase and injection of the solubilized material (Knudsen, *Anal. Biochem.* 147:285–288, 1985). The solid phase matrix may be solubilized in an appropriate organic solvent (e.g., DMSO) and either mixed with adjuvant or saline, or injected directly.

Alternatively, the basement membrane preparation may be injected in the absence of a solid matrix and/or adjuvant. Injection or implantation may be intraperitoneal, intra-foot pad, subcutaneous, intramuscular or intravenous, but preferably intraperitoneal. The animals may also be injected with antigen complexed with adjuvant, such as Freund's adjuvant. Single or multiple booster immunizations are used. Between one and seven days prior to the fusion date, preferably on days one through four, intravenous injections of the appropriate basement membrane preparation may be given daily.

Between one and seven days, preferably four days, after the administration of the final booster immunization, spleens or portions thereof are harvested from the immunized animals. At this time, the lymph nodes may also be harvested and included in the cell preparation. The harvested organs are minced using techniques which disrupt the structure of the organ, but which are not detrimental to the lymphocytes. The organs are preferably minced with scissors, passed through a mesh screen and mixed with growth medium to enrich the preparation for lymphocytes. The minced and strained tissue is harvested by centrifugation, then mixed with growth medium to form a cell suspension. The red blood cells may be lysed by adding a hypotonic or hypertonic solution to the cell suspension. A preferred method for cell lysis is to add distilled water to the suspensions and quickly return the suspensions to an isotonic state with a hypertonic sodium chloride solution. Any remaining tissue may be removed by filtration through gauze.

The harvested cell suspension is then mixed with a myeloma cell line, preferably one which is syngeneic with the immunized animal. Myeloma cell lines from various species are widely available through, for example, American Type Culture Collection, Rockville, Md. Myeloma cell lines commonly used include P3X63Ag8 (ATCC TIB 9), SP2/0-Ag14 (ATCC CRL 1581), FO (ATCC CRL 1646) and 210RCY-Ag1 (Galfre et al., Nature 277:131, 1979). A preferred cell line is P3/NS1/1-Ag4-1 hereinafter referred to as NS-1 (ATCC TIB 18). The NS-1 cells are preferably tested to determine the cloning efficiency of the strain. This may be accomplished by cloning out the NS-1 strain by limiting dilution and carrying out test fusions with the individual NS-1 clones to find candidates with the highest fusion efficiencies.

The myeloma cells are cultured in an appropriate mammalian cell growth medium, a variety of which are generally known in the art and available from commercial sources. Mammalian cell lines are routinely grown between 36° C. and 40° C. under conditions which maintain an optimal pH between 6.0 and 8.0, preferably about pH 7.2. pH may be maintained through the use of a variety of buffer systems known in the art. A preferred buffer system involves growing the cells in a bicarbonate buffer in a humidified incubator containing $CO_2$, preferably about 7% $CO_2$.

The fusion between the lymphocytes from the immunized animal and the myeloma cells may be carried out by a variety of methods described in the literature. These methods include the use of polyethylene glycol (PEG) (Brown et al., J. Biol. Chem. 255:4980–4983, 1980) and electrofusion (Zimmerman and Vienken, J. Membrane Biol. 67:165–182, 1982). An electrofusion generator is commercially available from Biotechnologies and Experimental Research, Inc., San Diego, Calif.

Following the fusion, the cells are plated onto multiwell culture plates, preferably 96-well plates. A reagent which selectively allows for the growth of the fused myeloma cells over the unfused cells is added to the culture medium. A preferred selection technique uses HAT (hypoxanthine, aminopterin, thymidine) selection. Other selection techniques may also be used depending on the myeloma cell line chosen.

Alternative methods of producing monoclonal antibodies utilize vitro immunization techniques. Lymphocytes may be harvested from lymphoid organs, such as spleen or lymph nodes, or from whole blood as peripheral blood lymphocytes. The lymphocytes are put into culture in the presence of the appropriate basement membrane preparation. Often immunostimulatory polypeptides will be added to the culture medium concurrently. At various times following the culturing of the lymphocytes in vitro, the lymphocytes are harvested and fused with a myeloma cell line as described above.

Other techniques for producing and maintaining antibody secreting lymphocyte cell lines in culture include viral transfection of the lymphocyte to produce a transformed cell line which will continue to grow in culture. Epstein barr virus (EBV) has been used for this technique. EBV transformed cells do not require fusion with a myeloma cell to allow continued growth in culture.

Thymocytes may be used as a feeder layer to condition the medium for the fused cells. Alternatively, peritoneal macrophages or non-immune spleen cells may be used as a feeder layer. Another alternative is to use conditioned medium from thymocytes or macrophages. Thymocytes may be prepared from juvenile mice less than 8 weeks old. The thymus glands are harvested and minced using techniques which disrupt the thymus gland but are not detrimental to the thymocytes. This procedure is preferably carried out using scissors to mince the tissue, followed by passage of the tissue through a mesh screen. The minced and strained cell material is then harvested by centrifugation. Cell suspensions are made using growth medium. Any remaining connective tissue may be removed by filtration through gauze.

At an appropriate time following the day the cells are fused, the fused cells (hybridomas) are then analyzed for the production of antibody against the antigen of choice. This "screening" can be done by a wide variety of techniques, including Western blot, ELISA, immunoprecipitation, affect on biological activity assays and immunocytochemical staining. These techniques and others are well described in the literature. (See, for example, J. G. R. Hurrell (ed.), Monoclonal Hybridoma Antibodies: Techniques and Applications, CRC Press Inc., Boca Raton, Fla., 1982.) Introduction of a screening procedure permits further definition of antibodies of useful reactivity. For example, basement membrane-derived materials purified from the urine of a representative disease, such as bladder cancer, may be used in any of the above-named techniques to define antibodies which react, for example, to determinants which are common to all patients, such as those functional in the physicochemical method noted above. Such antibodies may also be screened against intact, purified basement membrane components to discover whether the antibodies react with a neoantigenic determinant.

Hybridomas which secrete antibodies of interest are maintained in culture. The cells are expanded in culture and at the same time may be cloned in such a manner as to obtain colonies originating from single cells. This provides for the monoclonal nature of the antibodies obtained from the hybridomas. A wide variety of techniques exist for cloning cells, including limiting dilution, soft agar cloning and fluorescence-activated cell sorting.

Once clones of cells are obtained, they are reassayed for the production of the antibody of interest. These cells are then expanded in culture to allow for the production of larger amounts of the antibody. Methods for expansion of the cells include maintaining the cells in culture, placement of the cells in a bioreactor or other type of large-scale cell culture environment, or culturing the cells using various agar or gelatin carrier matrices. Antibodies are then isolated from the cell culture media.

A preferred method of producing large amounts of antibodies involves growing the hybridoma cells in the peritoneal cavity of syngeneic mice, thereby producing ascites fluid. The hybridomas are preferably isolated from the culture media by centrifugation and washed with an iso-osmotic solution, preferably phosphate buffered saline. The cells are then resuspended in an iso-osmotic solution and injected into the peritoneal cavity of an appropriate host animal, preferably a mouse, and allowed to grow within the host animal. The host animal may receive a pre-injection of pristane (2,6,10,14-tetramethylpentadecane) prior to the injection of the hybridoma cells, preferably seven to thirty days prior to the introduction of the hybridomas. Following growth of the cells in the peritoneal cavity, ascites fluid, containing the antibody of interest, is collected.

Antibodies may be purified from conditioned media or ascites fluid by a variety of methods known in the art. These methods include ammonium sulfate precipitation, ion exchange chromatography (see Hurrell, ibid.) and high pressure liquid chromatography using a hydroxylapatite support (Stanker et al., J. Immunol. Methods 76:157, 1985). A preferred method for purifying antibodies from conditioned media or ascites fluid utilizes a commercially available Protein A-Sepharose CL-4B column (Pharmacia, Piscataway, N.J.; Sigma, St. Louis, Mo.). Antibodies may be purified with these columns using conditions suggested by the manufacturer. Typically, the conditioned medium or ascites fluid is mixed with an equal volume of TNEN (20 mM Tris-base pH 8.0, 100 mM NaCl, 1 mM $Na_2EDTA$, 0.5% NP-40) and applied to the column. The antibodies are eluted using a low pH buffer. Preferably, the elution buffer comprises 0.1M sodium citrate, pH 3.5. Antibody-containing elements are immediately adjusted to pH 7.4, preferably using a saturated trisodium phosphate solution.

Detection of one or more immunocomplexes formed between a fragment, or complex, of one or more basement membrane components and an antibody specific for the fragment or complex may be accomplished by a variety of known techniques, such as radioimmunoassays (RIA) and enzyme linked immunosorbent assays (ELISA).

The immunoassays known in the art include the double monoclonal antibody sandwich immunoassay technique of David et al. (U.S. Patent No. 4,376,110); monoclonal polyclonal antibody sandwich assays (Wide et al., in Kirkham and Hunter (eds.), *Radioimmunoassay Methods*, E. and S. Livingstone, Edinburgh, 1970); the "western blot" method of Gordon et al. (U.S. Patent No. 4,452,901); immunoprecipitation of labeled ligand (Brown et al., *J. Biol. Chem.* 255:4980–4983, 1980); enzyme-linked immunosorbant assays as described by, for example, Raines and Ross (*J. Biol. Chem.* 257:5154–5160, 1982); immunocytochemical techniques, including the use of fluorochromes (Brooks et al., *Clin. Exp. Immunol.* 39: 477, 1980); and neutralization of activity (Bowen-Pope et al., *Proc. Natl. Acad. Sci. USA* 81:2396-2400, 1984), all of which are hereby incorporated by reference. In addition to the immunoassays described above, a number of other immunoassays are available, including those described in U.S. Pat. Nos.: 3,817,827; 3,850,752; 3,901,654; 3,935,074; 3,984,533; 3,996,345; 4,034,074; and 4,098,876, all of which are herein incorporated by reference.

For detection purposes, the antibodies may either be labeled or unlabeled. When unlabeled, the antibodies find use in agglutination assays. In addition, unlabeled antibodies can be used in combination with other labeled antibodies (second antibodies) that are reactive with the antibody, such as antibodies specific for immunoglobulin. Alternatively, the antibodies can be directly labeled. Where they are labeled, the reporter group can include radioisotopes, fluorophores, enzymes, luminescers, or dye particles. These and other labels are well known in the art and are described, for example, in the following U.S. Pat. Nos.: 3,766,162; 3,791,932; 3,817,837; 3,996,345; and 4,233,402.

Typically in an ELISA assay, antigen is adsorbed to the surface of a microtiter well. Residual protein-binding sites on the surface are then blocked with an appropriate agent, such as bovine serum albumin (BSA), heat-inactivated normal goat serum (NGS), or BLOTTO (buffered solution of nonfat dry milk which also contains a preservative, salts, and an antifoaming agent). The well is then incubated with a sample suspected of containing specific antibody. The sample can be applied neat, or, more often, it can be diluted, usually in a buffered solution which contains a small amount (0.1%-5.0% by weight) of protein, such as BSA, NGS, or BLOTTO. After incubating for a sufficient length of time to allow specific binding to occur, the well is washed to remove unbound protein and then incubated with an anti-mouse immunoglobulin antibody labeled with a reporter group. The reporter group can be chosen from a variety of enzymes, including horseradish peroxidase, beta-galactosidase, alkaline phosphatase, and glucose oxidase. Sufficient time is allowed for specific binding to occur, the well is again washed to remove unbound conjugate, and the substrate for the enzyme is added. Color is allowed to develop and the optical density of the contents of the well is determined visually or instrumentally.

In one preferred embodiment of the present invention, a reporter group is bound to the antibody. The step of detecting an immunocomplex involves removing substantially any unbound antibody and then detecting the presence or absence of the reporter group.

In another preferred embodiment, a reporter group is bound to a second antibody capable of binding to the antibody specific for a complex of one or more basement membrane components. The step of detecting an immunocomplex involves (a) removing substantially any unbound antibody, (b) adding the second antibody, (c) removing substantially any unbound second antibody and then (d) detecting the presence or absence of the reporter group. Where the antibody specific for the fragment is derived from a mouse, the second antibody is an anti-murine antibody.

In a third preferred embodiment for detecting an immunocomplex, a reporter group is bound to a molecule capable of binding to the immunocomplex. The step of detecting involves (a) adding the molecule, (b) removing substantially any unbound molecule, and then (c) detecting the presence or absence of the reporter group. An example of a molecule capable of binding to the immunocomplex is protein A.

It will be evident to one skilled in the art that a variety of methods for detecting the immunocomplex may be employed within the present invention. Reporter groups suitable for use in any of the methods include radioisotopes, fluorophores, enzymes, luminescers, and dye particles.

As noted above, the present invention also provides a physicochemical method for the detection of a disease that results in the release of fragments, intact molecules and/or complexes of one or more basement membrane components. This method, unlike the immunological method described above, is based upon the ability of molecules ("analytes") released by a disease into biological fluids to agglutinate a suspension of microparticles. In the case of cancers, for example, the analytes represent molecules which are released into a biological fluid as result of the metastatic process or the growth of a tumor and which agglutinate a suspension of microparticles.

The physicochemical method generally comprises contacting a biological fluid with a suspension of microparticles which agglutinate in the presence of fragments, intact molecules and/or complexes of basement membrane components. Subsequently, the presence or absence of agglutination of the suspension of microparticles is detected, thereby allowing the determination of the presence or absence of the disease. Representative diseases and biological fluids include those described above for the immunological method.

Microparticles suitable for use in this method include plastic latex, e.g., latex beads. Such a suspension of microscopic plastic particles is commonly prepared from polystyrene and derivatives thereof. The plastic may be in an underivatized form or in the form of derivatives, such as carboxylated or aminated. Typically, the microparticle has a diameter from about 0.01 to 5 microns, with about 0.25 microns preferred. It is advantageous to treat the suspensions of microparticles with one or more agents, such as bovine serum albumin, to block sites upon the surface of the particles which are available for nonspecific interactions.

The suspension of microparticles agglutinates in the presence of a biological fluid from a patient with a disease that results in the release of fragments, intact molecules and/or complexes of one or more basement membrane components. This agglutination reaction permits the detection of small amounts of basement membrane fragments, intact molecules or complexes in the presence of relatively large amounts of exogenous protein present in the biological fluid being tested. Thus, pretreatment of the biological fluid prior to testing is generally not required. In the case of biological fluids containing particulate contaminants, such as urine containing bacteria, cells, crystals, or other sediment, a brief centrifugation at low speeds sufficient to remove the particulate contaminants may be desirable.

It will be evident to one skilled in the art that a variety of methods for detecting the presence or absence of agglutination of a suspension of microparticles may be employed within the present invention. For example, a simple slide agglutination technique, such as those used extensively with small particle agglutination techniques, is suitable. In this technique, an aliquot of the suspension of microparticles is mixed with an aliquot of the specimen being tested on the surface of a glass slide. The reactants are mixed by rotating the slide manually or on a mechanical rotator. At time intervals, the appearance of the mixed reactants is judged relative to the appearance of the mixed reactants is judged relative to the appearance of a positive and negative control, which consists of known analyte-containing and non-analyte-containing specimen material, respectively. If, when viewed either macroscopically or microscopically, the unknown specimen being tested has caused agglutination of the microparticles in excess of that apparent in the negative control, the presence of an analyte in the unknown is established.

Other methods of determining the extent of aggregation of a suspension may also be used (e.g., as described by Cohen & Benedek, U.S. Pat. No. 4,080,264; Kraemer, *Am. J. Med. Tech.*, Vol. 48, No. 8, 1982; Looney, *J. Clin. Immun.* 7:90-95, 1984; and Grange et al., *J. Immun. Meth.* 18:365-375, 1977). Briefly, these include systems which detect the increase in rate of sedimentation of particles due to aggregation. Sedimentation may be judged visually or with the help f instrumentation which will record the increased rate of sedimentation by virtue of optical or other properties of the suspension. The distinctive light scattering properties of aggregates versus non-aggregated microparticles may be measured with a spectrophotometer or nephelometer set at any wavelength capable of measuring changes in these properties, e.g., 350, 660 or 700 nm.

To summarize the examples which follow, Example 1 describes several latex agglutination assays. Example 2 provides the purification of complexes of basement membrane components. Example 3 discloses the preparation of monoclonal antibodies to fragments and complexes of fragments of basement membrane components. Example 4 describes the identification of the antibodies produced. Example 5 provides the characterization of monoclonal antibodies. Example 6 discloses the large-scale culture of hybridomas.

The following examples are offered by way of illustration and not by way of limitation.

EXAMPLES

EXAMPLE 1

Latex Agglutination Assay

A. Reaction of Latex Reagent with Basement Membrane Components

To 750 ml of 49% suspension of 0.25 micron diameter carboxylated polystyrene latex (Morton-Thiokol, Morton International, Chicago, Ill.) is added 2 ml of goat serum from a healthy, unimmunized goat which has been diluted 1:10 in 0.85% saline. The mixture is placed in a 56° C. water bath for 60 minutes and stirred using a magnetic stirrer, or similar device, for 18-24 hours at room temperature. Seventy-five ml of this stock latex suspension is diluted 1:40 with 2925 ml of 0.005M Glycine Buffer (pH 8.2 containing 0.1% sodium azide) containing 4 g of bovine serum albumin (BSA). This latex suspension is mixed for two hours using a magnetic stirrer or similar device. The suspension is then adjusted to an Optical Density of 0.31 OD (Optical Density Standard) units at 700 nM, using distilled water as a blank, on a spectrophotometer to yield "latex reagent." The addition of 12 mg of human gamma globulin (in 20 ml of 0.85% saline) prior to the 56° C. heat step improves agglutinating activity.

The ability of the latex reagent to react with constituents of basement membrane, producing a visible agglutination may be observed by the preparation of solution of Type IV Collagen (Sigma Chemical Co., St. Louis, Mo.) or Laminin (Sigma).

Briefly, 1 mg of either of the above materials is dissolved in 0.05M acetic acid, and a 1/10 dilution prepared in 0.013M glycine buffer containing 0.075M NaCl is made to produce a working reagent of 100 µg/ml. The pH of this solution is adjusted to pH 7.0. Two-fold dilutions of this solution in this same buffer may be made, and 50 microliters of each dilution is placed within a circle or well on a black glass serology or similar slide. Fifty µl of the latex reagent is added to each drop of this solution, and the mixture is stirred to the outer edge of the circle using a clean plastic or other stirrer, and the slide rocked slowly for 2 minutes. The slide is examined visually for agglutination of latex particles, and the extent of agglutination may be graded 1, 2, 3 or 4, where no agglutination is 0 and strong agglutination is 4. A typical example of the results of this experiment is presented in Table 1.

TABLE 1

| Agglutination of Latex Reagent in the Presence of Some Constituent Molecules of the Basement Membrane | | | | | |
|---|---|---|---|---|---|
| [Presence of agglutination = (+); no agglutination = (−)] | | | | | |
| | Concentration (ug/ml) | | | | |
| Analyte | 50 | 25 | 12.5 | 6.5 | 0 |
| Type IV Collagen (Sigma, St. Louis, Mo.) | + | + | + | − | − |
| Laminin (Sigma, St. Louis, Mo.) | + | − | − | − | − |

Latex agglutination reactions were performed using mixtures of collagen with laminin and fibronectin. Concentrations of laminin and fibronectin were chosen such that they had no agglutination reaction on their own. These levels were then used in combination with each other and with collagen (20 µg/ml). As shown in FIG. 6, combinations of fibronectin and collagen, or laminin and collagen, react more strongly in the agglutination reaction than alone. In addition, the concentrations of laminin and fibronectin which did not agglutinate on their own, did when combined. Fibronectin, laminin and collagen when all combined showed a very strong reaction. This data further demonstrates the ability of the test to respond to basement membrane complexes more effectively than individual components.

B. Reaction of Latex Reagent with a Biological Fluid and Detection of Agglutination A convenient method for the detection of agglutination relies upon visual interpretation of agglutination of the latex against a dark background. This test procedure is performed by placing 50 microliters of serum or urine within a circle or well on a black glass serology or similar slide. Subsequently, approximately 50 microliters of the latex reagent from part A is placed on the drop of serum or urine in the circle or well. The mixture is stirred to the outer edge of the circle using a clean plastic or other stirrer, and rocked slowly for 2 minutes. The slide is examined visually for agglutination of the latex particles. An example of the results of this experiment as performed on the urine of individuals with and without bladder cancer, and the serum of individuals with and without non-small cell lung cancer, melanoma, and breast cancer is given in Table 2.

TABLE 2

Agglutination of Latex Reagent Exposed to the Urine or Serum of Individuals With and Without Several Types of Cancer

| Type of patient/ specimen | No of specimens | No. of specimens positive | No. of specimens negative |
| --- | --- | --- | --- |
| No cancer/urine (n = 968) | 968 | 49 | 919 |
| Transitional cell carcinoma of the bladder/urine (n = 97) | 97 | 65 | 32 |
| No cancer/serum (n = 974) | 974 | 86 | 888 |
| Non-small cell cancer of the lung/serum (n = 18) | 45 | 29 | 16 |
| Melanoma/serum (n = 12) | 29 | 22 | 7 |
| Breast cancer/ serum (n = 71) | 113 | 74 | 39 |

(n = number of patients)
(Note: In cases where n is less than the number of specimens tested, patients were retested over a period of months in a random fashion, without regard to previous test results.)

C. Time Course of Latex Agglutination with a Positive Urine Sample versus Type IV Collagen The latex reagent in this test is a 0.068% suspension of latex beads (0.17 micron) in a 0.13M glycine buffer (pH 8.5) with 0.1% sodium azide as a preservative. The beads are treated with blockers to help eliminate non-specific binding, before diluting with the glycine buffer. Forty µg of human gamma globulin fraction II, III (Sigma Chemical) diluted in 1 ml 0.85 NaCl to 100 ml of a 40% latex suspension (Lytron 601, 0.17 micron Morton Thiokol) is added. After mixing for ten minutes, 40 µl of normal goat serum (NGS, Sigma Chemical) diluted with 1 ml 0.85% NaCl is added. After mixing at room temperature for 2 hours, the latex suspension is placed in a 56° C. water bath for 2 hours. The latex suspension is removed from the water bath and mixed for 18-24 hours at room temperature.

Sixty ml of the stock latex suspension is added to 5 liters of 0.13M glycine buffer containing 100 mg of bovine serum albumin (BSA; purchased from Sigma Chemical) and 5 gm of sodium azide (Sigma Chemical). This working latex reagent is adjusted to pH 8.5 and mixed for 1 hour at room temperature. The working latex reagent is stored at 2° C.-8° C.

The test is performed by adding 25 µl of sample to assigned wells on a microtiter plate or strip. The latex reagent is mixed and 200 µl is dispensed to each well. The test is read on a microtiter plate or strip reader at 660 nm after standing at room temperature for 30 minutes. In the case of the experiment shown in FIG. 7, readings were made immediately and then at the time intervals designated.

The time course of a positive urine sample and collagen Type IV (20 µg/ml) are compared in FIG. 7. As can be seen, the rate of reaction of the positive urine sample is greater than with collagen alone, once more indicative that the basement membrane fragments are reacting in a cooperative manner.

EXAMPLE 2

Purification of Complexes of Basement Membrane Components

Urine showing latex test positivity, e.g., urine pooled from patients with bladder cancer is brought to 0.1% sodium azide by the addition of solid sodium azide, 0.005M iodoacetamide by the addition of solid iodoacetamide, and 0.005M phenylmethyl sulfonyl fluoride (PMSF) by the addition of 1M PMSF in absolute ethanol. EDTA is added to 0.025M. It is important that the urine be kept at approximately 4° C. following collection, and that the following steps are carried out at that temperature.

The urine is centrifuged at 1500×g for 10 minutes, and the supernatant is aspirated from the pellet, if any. The supernatant is concentrated approximately 40-50-×in a pressure concentrator using a low nonspecific binding molecular exclusion membrane with a MW cutoff of approximately 30,000 (for example, an Amicon YM-30 membrane).

The concentrated urine is chromatographed on an agarose gel column prepared from 8% agarose beads, 100-200 microns in size, equilibrated with 0.02M Tris HCl, 0.13M NaCl, 0.025M EDTA, and 0.002M Benzamidine, pH 7.8.

The fractions containing the majority of latex test-positive material are pooled and concentrated by pressure ultrafiltration using a low nonspecific binding ultrafiltration membrane with a MW cutoff of approximately 30,000 (for example, an Amicon YM-30 membrane). The resulting concentrate is rechromatographed on a 4% agarose column, having an approximate MW cutoff of 15 million, in the same buffer as for the 8% agarose column. Because this gel filtration step uses a resin with a capacity for sieving very high molecular weight compounds, some separation of immunoreactive material takes place.

The presence of material, for use in preparing antibodies, in subfractions of the effluent from the 8% or 4% agarose columns is determined by performing an ELISA for the constituent molecules of the basement membrane fragments, as well as by reacting aliquots of the subfractions with the microparticle aggregation assay, above. The ELISA reactivity of various fractions of urine from bladder cancer patients with antibodies to known basement membrane constituents (Sigma, St. Louis, Mo.; Telios, San Diego, Calif.; is summarized in Table 3.

TABLE 3

Reactivity of Subfractions of the Urine of Normal and Bladder Cancer Patients Fractionated According to Example 2

Solid phase antigen: subfractions of 4% agarose gel chromatography, according to Example 2

| Primary Antibody Specificity | Maximum Absorbance v. Background | | | |
|---|---|---|---|---|
| | Immunoreactive Peak I | | Immunoreactive Peak II | |
| | Patient 1 | Patient 2 | Patient 1 | Patient 2 |
| Type IV Collagen | 0.5 | (0) | 0.1 | (0) |
| Laminin | (0) | (0) | (0) | 0.25 |
| Fibronectin | (0) | 0.7 | 0.2 | (0) |

The ELISAs are performed by using microtiter plates adsorbed with subfractions of material eluted from agarose gel chromatography as solid phase. Briefly, subfractions at 2 μg/ml in ELISA buffer A (Table 5 in Example 3) are incubated in microtiter plates (100 μl well) overnight at 4° C. The plates are washed three times with ELISA buffer C (Table 5 in Example 3) and 100 μl anti-basement membrane constituent (e.g. anti-laminin or anti-collagen Type IV) antibody (the "primary" antibody) diluted to 1/1000 in ELISA buffer C is added, and the plates are incubated at 37° C. for 0-5 hours. The plates are then washed three times with ELISA buffer C. One hundred μl of a 1/1000 dilution, in ELISA buffer C, of antibody specific for the IgG of the species from which the primary antibody was derived, conjugated to horseradish peroxidase, is added, and the plates are incubated for 0.5 hour at 37° C. The plates are washed three times with ELISA buffer C, and 100 μl substrate (1 volume of 2 mg/ml N,N,N',N'-tetramethylbenzidine in methanol in 2 volumes ELISA buffer D) is added. Following incubation at room temperature for 10 to 20 minutes, the plates are read at either 380 nm in an ELISA plate reader (for example, Dynatech Laboratories, Inc., Alexandria, Va.) or at 450 nm after stopping the reaction with 1N sulfuric acid.

Figure 2:
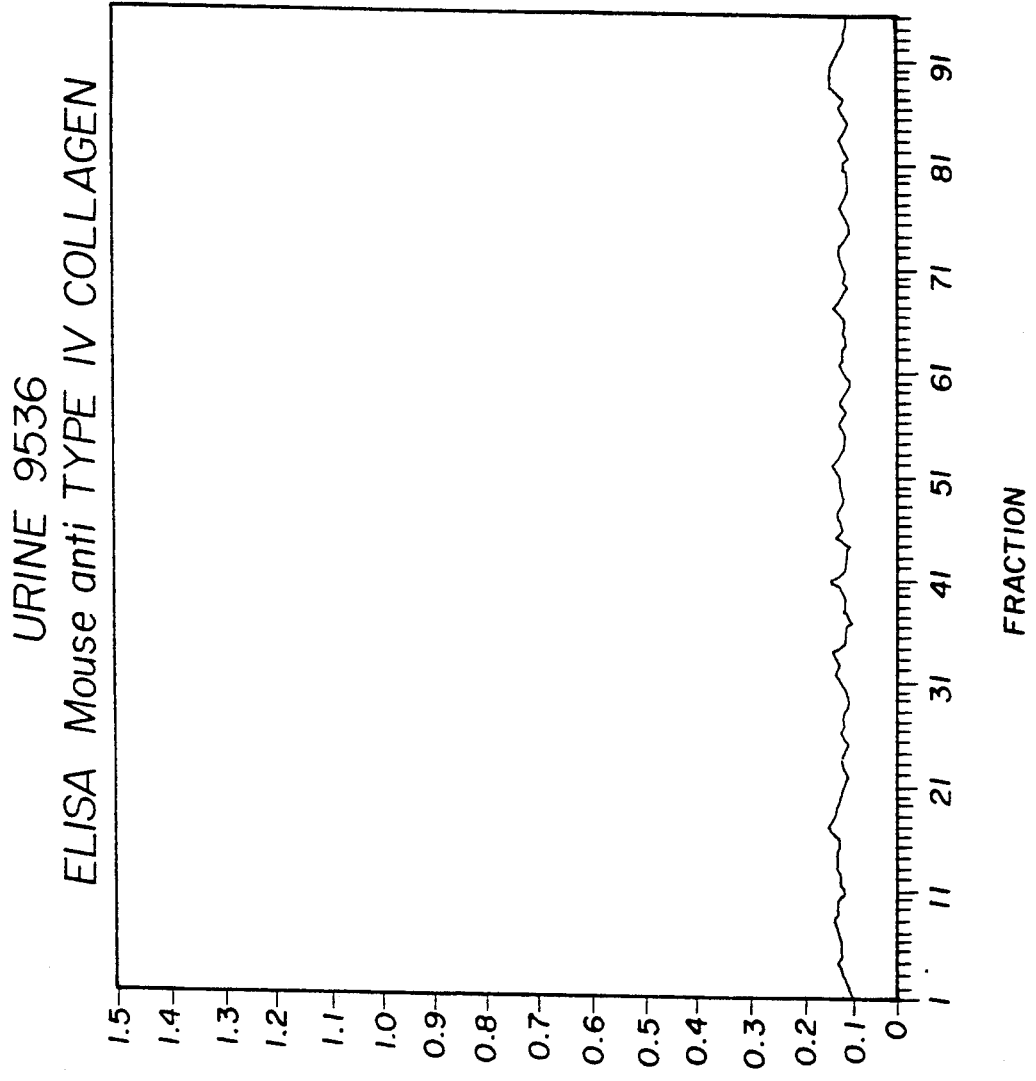
FIG. 2 is an elution profile of a normal individual's urine subjected to gel filtration chromatography on 4% agarose.

Additionally, when the unconcentrated urine of a bladder cancer patient is fractionated over an agarose gel column, basement membrane-derived material may be detected in the void volume peak (FIG. 1) when the effluent is tested by the ELISA method described above. Normal urine shows no such immunoreactivity when similarly treated (FIG. 2).

After fractionation on 4% agarose, latex agglutination reactive fractions were combined and dialyzed against 20 mM sodium phosphate buffer, pH 7.4. This material was then applied to a Heparin agarose (Sigma Chemical Company, St. Louis, Mo.) column (1×20 cm) which is equilibrated in the same buffer. This column was then sequentially eluted with 20 mM phosphate buffer (pH 7.4) containing 0, 50, 150 and 500 mM sodium chloride. Fractions eluting from the column were tested for latex slide activity. The agglutinating activity was found in both the fractions eluting at 150 mM and 500 mM sodium chloride as seen in FIG. 3. Cytokeratin, another marker associated with bladder cancer, was detected by ELISA using antibody clone 8.13 (Sigma Chemical Co., St. Louis, Mo.) in the 20 mM fraction and was clearly not associated with the agglutinating activity. Both of the latex agglutination reactive fractions (150 mM and 500 mM) were then concentrated on an Amicon PM10 membrane and dialyzed against 20 mM sodium phosphate buffer (pH 7.4) and applied separately to x 20 cm DEAE-Biogel A columns (Biorad, Richmond, Calif.). Fractions were again eluted using 20 mM phosphate buffer containing 0, 50, 150 and 500 mM sodium chloride. Fractions were then tested for agglutinating reactivity and tested in an ELISA assay with anti-Type IV collagen and anti-fibronectin antibodies.

The majority of the agglutinating activity in the 150 mM fraction from Heparin agarose also appeared in the 150 mM fraction from DEAE-Biogel A with a small portion of the activity in 500 mM fraction. The opposite was seen with the 500 mM Heparin agarose fraction after separation on DEAE-Biogel A. FIG. 4 shows the elution profile of the 500 mM Heparin agarose fraction after further purification on DEAE-Biogel A. Both the 150 mM and 500 mM DEAE fractions showed reactivity in the slide agglutination assay and were reactive with antibodies to both Type IV Collagen and fibronectin, indicative of these two proteins purifying as part of a complex.

When tested with the antibodies derived by screening against fragments or complexes from bladder cancer urine (4% agarose fraction) both the 150 mM and 500 mM fractions were found to be reactive with three monoclonal antibodies, clones 3G12C4, 4A3D1 and 3H2A1. This can be seen in FIG. 5 for the 150 mM fraction from DEAE. In contrast, these fractions, although reactive with an antibody to Type IV collagen, were only weakly reactive, and, in addition, showed weak reactivity with anti-laminin.

EXAMPLE 3

Preparation of Monoclonal Antibodies to Fragments and Complexes of Basement Membrane Components A. Immunization of Mice Eight-week-old male or female Balb/c mice are immunized with individual basement membrane fragments or complexes ("fragment/complex"). One to two micrograms of a purified fragment/complex is injected into the peritoneal cavity of the Balb/c mice. Alternatively, the mice are injected with 200 ul of the same immunogen emulsified in 1 volume of Freund's complete adjuvant (ICN Biochemicals, Costa Mesa, Calif.). Either procedure is repeated a total of four times at two-week intervals, excepting that in the case of adjuvant-treated mice, Freund's incomplete adjuvant is substituted for the complete adjuvant. Four days prior to the fusion date, the mice are intravenously injected with 100 ng purified fragment/complex. The immune response of mice immunized in this fashion is titrated by ELISA, using microtiter plates adsorbed with antigen purified from the urine of bladder cancer patients as immunogen. Mice showing a high titer (for example, in excess of 12,000) when assayed in this fashion may be used for fusion.

B. Preparation of Immunized Mouse Spleen and Lymph Node Cells

To prepare for the fusion between the immunized mouse cells and the mouse myeloma cell line, the spleens and lymph nodes of the immunized mice are removed and minced with scissors in a petri plate. The minced tissues are suspended in 10 ml RPMI 1640

(RPMI, Gibco, Lawrence, Mass.), and debris is allowed to settle for 5 minutes.

The supernatant is transferred to 50 ml centrifuge tubes. The cell suspensions are centrifuged for 10 minutes at $200 \times g$. The supernatants are discarded and the pellets are resuspended in 10 ml RPMI.

C. Preparation of Mouse Myeloma Cells

The NS-1 mouse myeloma cell line is used for the fusion.

TABLE 4

NS-1 Medum
For a 500 ml solution:
5 ml 100 mM sodium pyruvate (Irvine, Santa Ana, Calif.)
5 ml 200 mM L-glutamine (Gibco)
5 ml 100x Penicillin/Streptomycin/Neomycin (Gibco)
50 ml inactivated fetal calf serum (BioCell, Carson, Calif.)
1 g NaHCO$_3$
Add RPMI 1640 (Gibco, Lawrence, Mass.) to a total volume of 500 ml
Sterilize by filtration through a 0.22 um filter
HT Medium
50 ml NS-1 medium
1 ml 50 × HT supplement (Sigma, St. Louis, Mo.)
HAT Medium
50 ml NS-1 medium
1 ml 50 × HAT supplement (Sigma, St. Louis, Mo.)
Freezing Medium
8 ml NS-1 medium
1 ml fetal calf serum
1 ml DMSO
Mix the ingredients and make fresh for each freezing.

$1 \times 10^7$ cells from a growing NS-1 culture are used to inoculate a 75 cm$^2$ tissue culture flask containing 50 ml NS-1 medium. The flasks are incubated at 37° C., 7% CO$_2$, until the cells reached a density of at least $5 \times 10^5$ cells/ml.

The cells are then cut back to $2 \times 10^5$ cells/ml daily. One day before the fusion, two 75 cm$^2$ flasks containing 50 ml of cell culture are set up. The NS-1 cells are mixed with immunized mouse spleen cells and fused as described below.

D. Preparation of Thymocytes

Thymus glands obtained from baby mice are the source of the thymocytes which are used as a feeder layer to condition the culture media for the cell fusions. Thymus glands are obtained from three- to four-week-old Balb/c mice. The thymus glands are rinsed with NS-1 medium and minced in a petri dish. The minced tissues are suspended by 10 ml NS-1 medium and debris is allowed to settle for 5 minutes. The supernatant is transferred to a 50 ml centrifuge tube, and the cells are centrifuged for 10 minutes at $200 \times g$. The supernatants are discarded and the pellets resuspended in 10 ml NS-1 medium. Dilutions of the cell suspensions are counted using a hemacytometer. The yield from two thymus glands is routinely about 400 million cells. The cells are stored at room temperature until ready for use.

E. Fusion of Immunized Mouse Cells with NS-1 Cells

To prepare cells for fusion, cells from a NS-1 clone, grown as described above, are transferred to 50 ml centrifuge tubes and centrifuged for 10 min at $200 \times g$. The supernatants are discarded and the cell pellets are resuspended and combined in 10 ml RPMI. The cell suspension is counted with a hemacytometer to monitor the cell viability as determined by trypan blue exclusion. The cell viability is determined to be greater than 95%.

For fusion, $2.5 \times 10^7$ NS-1 clone cells are added to the immunized mouse spleen/nymph node cells (prepared as described above). The mixed cells are centrifuged for 10 minutes at $200 \times g$. The supernatant is removed by aspiration with a Pasteur pipet attached to a vacuum line.

The sedimented cells are gently suspended in 1 ml of a 40% polyethylene glycol (PEG) solution (Kodak, 1,450 average MW), made up in RPMI, and pH adjusted to pH 8.0 with 2% sodium bicarbonate. The suspension is centrifuged at $200 \times g$ at room temperature for 15 minutes. The supernatant is discarded and 10 ml RpMl medium is added to gently resuspend the pellet. The cells are centrifuged at $200 \times g$ for 5 minute, and the supernatant is gently aspirated and discarded. 45 ml of HAT medium is added to the cell pellet, and the cells are gently resuspended. $5 \times 10^7$ thymocytes (prepared as above) are added to the cell suspension, and this final suspension is transferred to two 96-well culture plates at 200 ul per well. The plates are incubated at 37° C. in a humid incubator with 7% CO$_2$. The plates are examined microscopically after three days to determine fusion efficiency with the expectation of approximately five hybridoma colonies per well. The cells are fed after seven days by replacing 100 ul of the medium with fresh NS-1 medium containing $1 \times$ HAT and $2.5 \times 10^6$ thymocytes per ml. The hybridomas are tested between days 9 and 14 for the production of specific antibodies. Select hybridomas are chosen for further characterization.

EXAMPLE 4

Identification of the Antibodies Produced

Hybridomas from cell fusions are tested for the production of antibodies to a basement membrane fragment or complex. Assays used for identification of positive hybridomas include enzyme linked immunosorbent assays (ELISA), radioimmunoprecipitation (RIP) assays, and Western blots.

A. Screening fusions by ELISA

The ELISA assays are carried out in 96-well microtiter plates which has been coated with a fragment or complex purified form urine as described above. The microtiter plates used for assaying fusions are coated with 2 micrograms/ml fragment/complex. To coat the wells, fragment/complex is diluted to the appropriate concentration in ELISA buffer A (Table 5) and 100 ul of the fragment/complex solution is added to each well. The plates are incubated overnight at 4° C.

TABLE 5

ELISA Buffer A
0.1M NaHCO$_3$, pH 9.6
0.02% NaN$_3$
ELISA Buffer B
This buffer may be made with 1% or 2% bovine serum albumin (BSA, Sigma, St. Louis, Mo.)
5 or 10 g BSA (for 1% or 2% BSA, respectively)
250 ul Tween 20 (Sigma, St. Louis, Mo.)
100 mg NaN$_3$
Add phosphate-buffered saline pH 7.2 (PBS, Sigma St. Louis, Mo.) to a final volume of 500 ml. Alternatively, the buffer may be made up as 1% or 2% BSA in ELISA Buffer C.
ELISA Buffer C
0.04 g NaH$_2$PO$_4$
0.27 g Na$_2$HPO$_4$
0.05 g NaN$_3$ TABLE 5-continued 8.50 g NaCl
1.00 g BSA
0.5 ml Tween-20
and made up to 1 l with distilled $H_2O$.
ELISA Buffer D
0.1M Citric acid, pH-adjusted to 5.5 with NaOH
PBS
0.02M sodium phosphate pH 7.4
0.15M NaCl
0.5% $NaN_3$
Adjust the pH to 8 with concentrated HCl.

The ELISA assay is carried out on microtiter plates, prepared as described above, which have been washed three times with ELISA buffer C. 100 ul hybridoma culture supernatant is added to each test well. The plates are incubated for 0.5 hour at 37° C. After incubation, the plates are washed three times with ELISA Buffer C. The wells are then incubated for 0.5 hour at 37° C. with 100 ul of horseradish peroxidase-conjugated rabbit anti-mouse IgG (Sigma, St. Louis, Mo.). The wells are then washed three times with ELISA Buffer C. After the wash step 50 ul of substrate, containing 1 volume 2 mg/ml N,N,N,N'-tetramethylbenzidine in methane (Sigma, St. Louis, Mo.) in two volumes ELISA Buffer D, is added to each well and the plates are incubated for 10 to 20 minutes at room temperature. The plates are then scored using a Dynatech ELISA plate reader (For example, Dynatech Laboratories, Inc., Alexandria, Va.) using a filter to monitor absorbance at 380 nm. Those wells with $A_{380}$ readings significantly greater than blank substrate value are taken as positives.

The positive candidates are re-assayed by ELISA assay as described above. These samples are assayed in duplicate with microtiter plates coated with 1 μg/ml fragment/complex or which have been incubated with ELISA Buffer A alone. Positive results shown by the candidates on the latter plates (coated with Buffer A alone) indicate nonspecific binding to plastic. Candidates which show significant reactivity on ELISA plates coated with fragment/complex and insignificant reaction against the plastic are chosen for cloning and characterization.

B. Cloning of Hybridomas

Hybridomas shown to be positive through both the ELISA and RIP screens are cloned twice by limiting dilution and screened by ELISA to isolate and assure the monoclonality of the hybridomas. The cloning by limiting dilution plating is carried out as follows. The parental wells are diluted with NS-1 medium to a concentration of 5 cells per ml of culture medium. The cell mixture is then plated into 96-well culture plates at 200 ul per well, averaging approximately 1 hybridoma cell per well. After seven days in culture, the wells are individually scanned microscopically to screen for wells containing single colonies of cells.

Those wells containing single colonies are assayed by ELISA, using fragment/complex as the antigen, for the presence of specific antibodies in the conditioned media.

Cells positive for antibody production are expanded in culture to obtain large amounts of the monoclonal antibodies. Cells found to be positive for antibody production following the first round of cloning are candidates for a second round. One clone obtained for each of the hybridomas is then subjected to a second round of cloning by limiting dilution, using conditions identical to those described above.

EXAMPLE 5

Characterization of Monoclonal Antibodies

Positive hybridoma candidates are tested for the ability to bind the fragment or complex isolated from various subfractions of agarose gel chromatography as described in Example 2 above, as well as purified basement membrane constituent molecules. The assays are carried out by ELISA, using as solid phase microtiter plates adsorbed with various subfractions of agarose gel chromatography identified as containing fragments of basement membrane, and microtiter plates adsorbed with constituent molecules of basement membrane, for example, Type IV collagen (Sigma, St. Louis, Mo.) to identify antibodies prepared against fragment/complex from the urine of bladder cancer patients which are nonreactive with known basement membrane constituents. ELISA is otherwise carried out according to the procedure explained in Example 4, above. The reaction pattern of a monoclonal so characterized is summarized in Table 6.

TABLE 6

| Characterization of Monoclonal Antibody 3H2A1 | |
|---|---|
| Reactivity to: | Absorbance vs. Blank |
| Latex reactive peak I, 8% agarose gel chromatography | 1.25 |
| Latex reactive peak II, 8% agarose gel chromatography | (0) |
| Human placental type IV collagen | 1.5 |

EXAMPLE 6

Large-Scale Culture of Hybridomas

Following identification and characterization of the antibodies, the hybridomas are cultured for the production of large quantities of antibodies. This large scale production of antibodies is carried out by culturing the hybridomas in ascites as described below.

Balb/c mice are injected intraperitoneally with 1 ml of Pristane (2,6,10,14-tetramethylpentadecane, Aldrich Chemical, Milwaukee, Wis.) between seven and ten days before being injected with the hybridomas. The mice are injected intraperitoneally with approximately $5 \times 10^6$ cells per mouse.

Ascites fluid is removed from the mice with an 18 gauge needle between seven and ten days after injection. Any cells and/or cell material are removed from the ascites fluid by centrifugation.

Antibodies are purified from ascites fluid using a protein A-Sepharose CL-4B (Sigma, St. Louis, Mo.) column equilibrated with TNEN. The ascites fluid is mixed with an equal volume of TNEN buffer. The solution containing the ascites is then applied to the column and cycled over the column two times. The column is washed with three to four column volumes of TNEN and bound material is eluted with 0.1M sodium citrate, pH 3.0. Fractions are collected, neutralized by the addition of 1.5 M Tris-base, pH 8.5, and the absorption at 280 nm is monitored. Peak fractions are pooled and the protein concentration is determined by adsorption at 280 nm using a extinction coefficient of 1.4 for a 1 mg/ml solution.

From the foregoing, it will be appreciated that, although specific embodiments of the invention have been described herein for purposes of illustration, various modifications may be made without deviating from the spirit and scope of the invention.

We claim:

1. A method for the detection of a cancer that results in the release of fragments, intact molecules and/or complexes of one or more basement membrane components, comprising the steps of:
    contacting a biological fluid with a suspension of latex beads which are treated with a blocking agent and which agglutinate in the presence of fragments, intact molecules and/or complexes of basement membrane components, said agglutination not being due to a specific antibody-antigen interaction; and
    detecting the presence of absence of agglutination of said suspension of latex beads, thereby determining the presence or absence of said cancer.

2. The method of claim 1 wherein the cancers are selected from the group consisting of urogenital, melanoma, lung and breast cancers.

3. The method of claim 1 wherein the biological fluid is selected from the group consisting of urine, serum, synovial fluid, and cerebrospinal fluid.

4. The method of claim 1 wherein the latex beads are additionally treated with human gamma globulin.

5. A method for detecting the presence of complexes of basement membrane components in a sample, comprising the steps of:
    contacting a sample with a suspension of latex beads which are treated with a blocking agent and which agglutinate in the presence of complexes of basement membrane components, said agglutination not being due to a specific antibody-antigen interaction interaction; and
    detecting the presence or absence of agglutination of said suspension of latex beads, thereby determining the presence or absence of said complexes in said sample.

6. The method of claim 5 wherein the latex beads are additionally treated with human gamma globulin.

* * * * *

UNITED STATES PATENT AND TRADEMARK OFFICE
CERTIFICATE OF CORRECTION

PATENT NO. : 5,264,370
DATED : November 23, 1993
INVENTOR(S) : Morgan V. Aken and Stefan L. Paskell It is certified that error appears in the above-identified patent and that said Letters Patent is hereby corrected as shown below:

In column 21, claim 1, line 16, after "presence" and before "absence", please delete "of" and substitute therefor --or--.

In column 22, claim 5, lines 13 and 14, please delete the second "interaction".

Signed and Sealed this

Twenty-fourth Day of May, 1994

Attest:

BRUCE LEHMAN

Attesting Officer        Commissioner of Patents and Trademarks

UNITED STATES PATENT AND TRADEMARK OFFICE
CERTIFICATE OF CORRECTION

PATENT NO. : 5,264,370
DATED : November 23, 1993
INVENTOR(S) : Morgan Van Aken and Stefan L. Paskell It is certified that error appears in the above-identified patent and that said Letters Patent is hereby corrected as shown below:

On the title page, after the subheading, "Inventors", please delete "Morgan V. Aken" and substitute therefor --Morgan Van Aken--.

Signed and Sealed this

Twentieth Day of September, 1994

Attest:

BRUCE LEHMAN

*Attesting Officer*     *Commissioner of Patents and Trademarks*